(12) United States Patent
Thomson et al.

(10) Patent No.: US 9,364,014 B2
(45) Date of Patent: Jun. 14, 2016

(54) PROCESS OF PRODUCING TOMATO PASTE

(75) Inventors: Helen Elizabeth C. Thomson, Sharnbrook (GB); Jose Anisio Castilho, Valinhos (BR)

(73) Assignee: Nunhems B.V., Nunhem (NL)

( * ) Notice: Subject to any disclaimer, the term of this patent is extended or adjusted under 35 U.S.C. 154(b) by 355 days.

(21) Appl. No.: 12/593,618

(22) PCT Filed: Mar. 7, 2008

(86) PCT No.: PCT/EP2008/052778
§ 371 (c)(1),
(2), (4) Date: Sep. 29, 2009

(87) PCT Pub. No.: WO2008/119618
PCT Pub. Date: Oct. 9, 2008

(65) Prior Publication Data
US 2010/0104728 A1 Apr. 29, 2010

(30) Foreign Application Priority Data
Mar. 30, 2007 (EP) .................................. 07105340

(51) Int. Cl.
A23L 1/212 (2006.01)
A23L 1/24 (2006.01)

(52) U.S. Cl.
CPC ............... *A23L 1/2128* (2013.01); *A23L 1/243* (2013.01); *A23V 2002/00* (2013.01)

(58) Field of Classification Search
CPC ........... A23V 2002/00; A23V 2200/30; A23V 2250/038
USPC .......................... 426/552, 573, 589, 518, 392
See application file for complete search history.

(56) References Cited

U.S. PATENT DOCUMENTS

| | | | | |
|---|---|---|---|---|
| 4,437,934 A * | 3/1984 | Nelson et al. | ................. | 159/47.1 |
| 2003/0046732 A1 | 3/2003 | Kinnersley | | |
| 2003/0224100 A1 | 12/2003 | de la Cuadra | | |
| 2004/0194634 A1* | 10/2004 | Succar et al. | .................... | 99/324 |
| 2007/0048353 A1 | 3/2007 | Monma | | |
| 2010/0331349 A1 | 12/2010 | Ley et al. | | |

FOREIGN PATENT DOCUMENTS

| | | |
|---|---|---|
| EP | 1211926 | 11/2003 |
| WO | 01/13708 A | 3/2001 |
| WO | WO0113708 A1 | 3/2001 |
| WO | WO 0113708 A1 * | 3/2001 |
| WO | 2004/017760 A | 3/2004 |
| WO | WO2004017760 A1 | 3/2004 |
| WO | WO 2004017760 A1 * | 3/2004 |
| WO | WO2005096841 | 10/2005 |
| WO | 2006/030445 A | 3/2006 |
| WO | WO2006030445 A2 | 3/2006 |

OTHER PUBLICATIONS

Growing Tomatoes, obtained from www.growtomatoes.com, pp. 7, date Jul. 8, 2008. Date verified by web.archive.org.*
Bhattarai et al., . "Effect of Harvesting Method and calcium on Post Harvest Physiology of Tomato", Nepal Agric. Res. J. vol. 7, 2006, pp. 37-41.*
Yilmaz et al "Chemistry of Fresh tomato flavor" turk J. Agric. For 25 (2001) 149-155.*
Anthon et al., Changes in pH, acids, sugars and othe quality parameters during extended vine holding of ripe processing tomatoes; J. Sci. Food Agric(2011), pp. 7.*
Abe Y., et al., Am. J. Hypertens. 3(1): 74-79.
Kimura M., et al., (Yakult) (2002), Japanese Journal of Pharmacoiogy 89(4): 388-94.
Owens, D.F. & Kriegstein, A.R. (2002), Nature Neuroscience 3:715-727.
Gordon F and Sved A (2002), Clin. Exp. Pharmacol. p. 29:522-524.
Leventhal A., et al. (2003).
European Search Report, EP 07 10 5340, dated Jul. 23, 2007, 3 pp.
JP 04 051878 A, Kagome, Feb. 20, 1992, Abstract.
Bernacchi et al., Advanced backcross QTL analysis in tomato—Identification of QTLs for traits of agronomic iportance from Lycopersicon hirsutum, Theor Appl Genet, 1998, pp. 381-397, vol. 97.
Bernachhi et al., An interspecific backscross of Lycopersicon esculentum x L. hirsutum: Linkage Analysis and a QTL study fo sexual compatibility factors and floral traits, Genetics, 1997, pp. 861-877, vol. 147.
Davies et al., The constituents of tomato fruit—the influence of environment, nutrition, and genotype, CRC critical reviews in food science and nutrition, Nov. 15, 198, pp. 205, 235, 236, 271.
Eshed et al., An Introgression Line Population of Lycopersicon pennellii in the Cultivated Tomato Enables the Identification and Fine Mapping of Yield-Assoc QTL, Genetics, Aug. 11, 1995, 1147-1162, 141, US.
Grandillo et al., Genetic improvement of processing tomatoes: A 20 years perspective, Euphytica, Apr. 27, 1999, 85-97, 110, US.
Hoff et al., The Effect of Nitrate & Ammonium Nitrogen on the Free Amino Acid Composition of Tomato Plants and Tomato Fruit, J Amer Soc Hort Sci, Jan. 1, 1974, 27-30, 99, US.
Kader et al., Amino Acid Composition and Flavor of Fresh Market Tomatoes as Influenced by Fruit Ripeness When Harvested, J Amer Soc Hor Sci, Jan. 9, 1978, 541-544, 103(4), US.

(Continued)

*Primary Examiner* — Jyoti Chawla
(74) *Attorney, Agent, or Firm* — Arent Fox LLP

(57) ABSTRACT

The present invention relates to a method of producing tomato pastes that have increased dietary value, e.g. resulting from the presence of a significant amount of gamma-aminobutyric acid. More in particular, the present method concerns producing tomato pastes from dehydrated processing tomatoes, said dehydrated tomatoes being obtained either by harvesting post-ripened tomatoes that have dehydrated while still on the vine or by harvesting tomatoes that are subsequently dehydrated by drying the intact tomatoes said tomatoes having a cuticle that is permeable to water. The inventors have observed that in order to produce a tomato paste with the desired high GABA content and optimum taste, the processing tomatoes should be dehydrated to a Brix value within the range of 5-10.

20 Claims, No Drawings

(56) References Cited

OTHER PUBLICATIONS

Kinnersley et al., Gamma Aminobutyric Acid (GABA) and Plant Responses to Stress, Critical Reviews in Plant Sc, Jan. 1, 2000, 479-509, 19 (6), US.
Okitani et al., Heat-induced Changes in Free Amino Acids on Manufacturing Heated Pulps, Purees & Pasts from Tomatoes, J Food Sci, Jan. 1, 1983, 1366-1367, 48, US.
Saito et al., Screening for 7-aminobutyric Acid (GABA)-rich Tomato Varieties, J Japan Soc Hort Sci, Jan. 1, 2008, 242-250, 77(3), JP.
Schauer et al., Comprehensive metabolic profiling & phenotyping of interspecific introgression lines for tomato improvement, Nature Biotech, Jan. 1, 2006, 447-454, 24, US.
Yelle et al., Sink Metabolism in Tomato Fruit, Plant Physiol, Jan. 1, 1991, 1026-1035, 95, US.
Opposition of EP 08 71 7525.3/ Patent EP 2 131 662, by Tomaisins International Ltd., Patentee Unilever N.V., Unilever PLC, Nov. 2, 2012.
Opposition of EP 08 71 7525.3/ Patent EP 2 131 662, Summons to attend oral proceedings pursuant to Rule 115(1) EPC, Mar. 10, 2014, 6 pp.
Program of the Poster Session, Mar. 25, 2007, pp. 1-6. Relating to Poster 101 from a meeting of the Japanese Society for Horticultural Science dated Mar. 25, 2007, JP.
Appeal Brief, Opposition in EP2131662 (EP08717525.3) Appeal Brief, 2006, pp. 1-12.
Opposition Brief Against EP1211926, Opposition Brief in EP2131662 (EP08717525.3) against EP1211926, Oct. 2, 2014, pp. 1-14.
A.J. Monforte et al., Comparison of a set of allelic QTL-NILs for chromosome 4 of tomato: Deductions about natural variation and implications for germplasm utilization, Theor Appl Genet, 2001, pp. 572-590, vol. 102.
C.M. Rick, Tomato Genetics Resource Center, TGRC, 2014, Accession LA3475; Cultivar Name: M-82.
Decision of the Opposition Division in EP1211926, Decision of the Opposition Division in EP1211926, May 29, 2006, pp. 1-14.
Dr. Zohar Nir, Declaration of Dr. Zohar Nir, Opposition in EP2131662, Oct. 2, 2014, pp. 1-5 (including 2 Annexes).
Matsukura et al., Screening of tomato varieties for high-GABA fruit and evaluation, Poster 101 From a Meeting of the Japanese Society, 2014, JP.
Nicolas Schauer et al., Metabolic profiling of leaves and fruit of wild species tomato: a survey of the Solanum lycopersicum complex, Journal of Experimental Botany, 2004, pp. 297-307, vol. 56 No. 410.
Notice of Opposition in EP2131662 (EP08717525.3), Oct. 11, 2012.
Yuan K. Liu and Bor S. Luh, Effect of Harvest Maturity on Free Amino Acids, Pectins, Ascorbic Acid, Total Nitrogen and Minerals in Tomato Pastes, Journal of Food Science, 1979, pp. 425-434, vol. 44.

\* cited by examiner

PROCESS OF PRODUCING TOMATO PASTE

FIELD OF THE INVENTION

The present invention relates to the field of tomato pastes that are used to prepare edible tomato products, such as ketchup and paste sauces and the like. More in particular, the present invention provides a new method of producing tomato pastes that have increased dietary value, e.g. resulting from the presence of a significant amount of gamma-aminobutyric acid.

BACKGROUND OF THE INVENTION

γ-Amino butyric acid (GABA) is an amino acid conserved from bacteria to plants. It is found in all known plant tissues and the metabolic pathways of GABA synthesis and turnover are well established for the majority of plants. In most cases, GABA is synthesised from glutamate by irreversible action of the enzyme glutamate decarboxylase (GAD). The production of GABA via the GABA shunt is heavily intertwined within the highly regulated and well-studied glutamate pathway. The physiological role of GABA in higher plants has been the subject of much debate.

Dietary intake of GABA is gaining attention due to the fact that it has been associated with a variety of beneficial physiological effects. According to the World Health Organisation, about two thirds of strokes and half the incidence of heart disease are attributable to raised blood pressure. Several studies have suggested that intake of GABA can lower blood pressure and there are claims that ingestion of GABA-rich plants can reduce blood pressure in hypertensive rats (Abe Y et al. (1995). Effect of green tea rich in gamma-amino butyric acid on blood pressure of Dahl salt-sensitive rats. Am. J. Hypertens. 8(1): 74-79). In another more recent study with hypertensive rats a dose of 0.3 to 1.0 mg/kg intra-duodenally administered GABA had a dose-related hypotensive effect, decreasing the blood pressure from 9.20+/−3.96 to 3.50+/−5.34 mmHg (Kimura M, et al., (Yakult) (2002). Involvement of gamma-amino butyric acid (GABA) B receptors in the hypotensive effect of systemically administered GABA in spontaneously hypertensive rats. Japanese Journal of Pharmacology 89(4): 388-94).

GABA is possibly associated with several other health benefits. It is known to be the major inhibitory neurotransmitter in the central nervous system and is therefore thought to have calming properties (Owens, D. F. & Kriegstein, A. R. (2002). Is there more to GABA than synaptic inhibition? Nature Neuroscience 3:715-727). Tea is well known for its relaxing properties, thought to be due to the naturally high levels of GABA (in combination with theanine) "GABA tea" was developed in Japan in 1986 and consists of green tea (naturally higher in GABA) with extra GABA added for relaxation and general well-being.

A diet high in GABA may also have implications for the treatment of the sensory, motor and cognitive declines that accompany old age because GABA modulates neurotransmitter release in the central and peripheral nervous systems (Gordon F and Sved A (2002). Neurotransmitters in central cardiovascular regulation: Glutamate and GABA. Clin. Exp. Pharmacol. P. 29: 522-524). In a recent study, older monkeys that had GABA directly delivered to their neurones responded to visual patterns in the same way as younger monkeys. The study mentions that normal ageing may therefore result in a decreased ability to produce GABA in the cerebral cortex, although this hypothesis is untested (Leventhal A. Et al. (2003). GABA and its agonists improved visual cortical function in senescent monkeys).

Consumers are becoming increasingly aware of the benefits of drinking green tea but may not necessarily associate this with GABA. A number of web-sites advertise health supplements that are high in GABA for lowering blood pressure, decreasing body fat and anxiety relief. Yakult® has launched a milk drink containing GABA known as "Pretio" in Japan (although this is not thought to be present elsewhere in the world) and Lion Corp has recently unveiled a functional beverage known as "Gussumin" based on tomato vinegar derived from fermented tomatoes rich in GABA to target female consumers with sleeping difficulties.

US 2007/0048353 discloses a method of producing food and beverage products with a high content of GABA, wherein processed tomato products are fermented with lactic acid bacteria.

Although most consumers will not be aware of the benefits of GABA, it is envisaged that as consumer awareness grows, there will be an increasing demand for other functional foods high in GABA.

Tomatoes are relatively high in GABA, compared to fresh tea leaves and many other fruit and vegetables, with some varieties being higher than others. Despite existing knowledge of the GABA shunt, up-regulation of GABA in fruits has mainly been achieved through environmental influences, which are difficult to control on a commercial scale.

It is an object of the present invention to provide a process of producing tomato pastes that are high in GABA and that can suitably be used to produce edible processed tomato products that fit into diets that aim to reduce blood pressure, to instil calmness and relaxation and/or to improve sensory, motor and/or cognitive functions.

SUMMARY OF THE INVENTION

The present inventors have found that this objective can be met by producing tomato pastes from dehydrated processing tomatoes, said dehydrated tomatoes being obtained either by harvesting post-ripened tomatoes that have dehydrated while still on the vine or by harvesting tomatoes that are subsequently dehydrated by drying the intact tomatoes. More in particular, the present inventors have found that tomato pastes meeting the aforementioned requirement can be produced from dehydrated tomatoes that have a cuticle that is permeable to water. Tomatoes comprising a water permeable cuticle offer the advantage that they can be left on the vine to dehydrate or, alternatively, that they can be dehydrated relatively easily by subjecting them to a drying treatment.

The inventors have observed that in order to produce a tomato paste with the desired high GABA content and optimum taste, the processing tomatoes should be dehydrated to a Brix value within the range of 5-10. If the processing tomatoes are not dehydrated or insufficiently dehydrated, the GABA level in the resulting tomato paste is unsatisfactory. If on the other hand the processing tomatoes are dehydrated to a Brix value above 10, the taste of the resulting tomato paste is poor. This poor taste is believed to result from decreased levels of glutamic acid and/or citric acid.

It is generally recognized in the art that the ripening process of fruits, and in particular that of tomato fruits, involves changes in cell wall composition thereof, especially cell wall polysaccharide degradation, e.g. by polygalacturonases, glucanohydrolase, pectin methyl esterases, pectate lyases and glycosidase. This process is normally referred to as fruit softening. A skilled person would expect this fruit softening to continue when the processing tomatoes are left to dehydrate. Furthermore, said skilled person would expect that these softened tomatoes would yield a tomato paste of inferior quality, especially in terms of rheological properties. As will be illustrated hereafter, however, it was unexpectedly found that the pastes obtained in accordance with the present invention do not suffer from deteriorated rheological properties.

WO 01/13708 discloses tomato varieties that have been produced by crossing at least one *Lycopersicon esculentum* plant with a *Lycopersicon* spp, to produce hybrid species that give rise to tomato fruits that can be left on the vine post-ripening to dehydrate, which is generally unaccompanied by microbial spoilage. The tomato fruits disclosed in WO 01/13708 are so called cherry tomatoes. Cherry tomatoes differ from processing tomatoes in that they are much smaller (typical diameter is 2.0-3.0 cm) and in that the fully ripened fruit has a substantially higher Brix value. Cherry tomatoes are not particularly suitable for producing tomato pastes that can be used in food products, as they do not provide satisfactory rheology, as is, for example, apparent from a high Bostwick value. The shape of cherry tomato fruit is usually globular to slightly elliptical (i.e. fruit width and fruit length are about equivalent).

Because of their small size and high initial Brix content, cherry tomatoes dehydrate rapidly to achieve high Brix levels when left on the vine. The examples of WO 01/13708 show that cherry tomatoes having an initial Brix value of about 11 can be naturally dehydrated while attached to the tomato plant to a Brix value of up to 29.

DETAILED DESCRIPTION OF THE INVENTION

Accordingly, a first aspect of the invention concerns a method of producing a tomato paste, comprising the steps of harvesting processing tomatoes, and comminuting or macerating said tomatoes, wherein, prior to comminuting or macerating, the harvested processing tomatoes have either been dehydrated on the vine to a Brix value in the range of 5-10 or wherein, following harvesting and prior to comminuting or macerating, the harvested processing tomatoes have been dehydrated to a Brix value within the range of 5-10, and wherein said tomatoes have a skin or cuticle which is water permeable. Another aspect of the invention concerns tomato pastes that are obtainable by this process.

The term "comprising" whenever used in this document is intended to indicate the presence of stated features, integers, steps, components, but not to preclude the presence or addition of one or more other features, integers, steps, components or groups thereof.

The term "Brix value" which is considered to be synonymous to the term Degrees Brix (symbol ° Bx) is a measure of the percent total soluble solids in a given weight of plant juice, which include the summation of sucrose, fructose, vitamins, amino acids, protein, hormones and other solids. It is often expressed as the percentage of sucrose. It is measured with a saccharimeter that measures specific gravity of a liquid or more easily with a refractometer or a Brix hydrometer. In accordance with the present invention the Brix value of the tomatoes is preferably determined using a refractometer. Methods of determining the Brix value of a tomato employing a refractometer are generally known in the art. For comparing compositions of different products having different Brix values, said products may first be brought to the same Brix level by concentration or dilution and subsequently be analysed or, alternatively, said different products may be analysed at their respective Brix values and the data may subsequently be corrected for the difference in Brix value. Both options are common and well known in the art. In this document, any statements regarding the contents of the tomatoes and tomato pastes will include the respective Brix value, unless it is on a dry solids weight basis.

The present invention specifically concerns a process wherein processing tomatoes are used. As is generally known in the art, 'fresh-market tomatoes' that are sold directly to consumers differ from those used for the production of processed tomato food products. Such tomatoes are relatively juicy and soft and the plants they grow on are in general of a variety of the indeterminate type. This means that the plants do not flower at the same time and fruits are not ripe simultaneously. Hence, a plant may contain unripe green fruits and ripe fruit at the same time. During culturing, the plants are generally grown as a cordon and grow during an extended period of e.g. 9 to 12 months. For industrial purposes, processing tomatoes should fulfil specific requirements, and therefore differ from tomatoes sold as fresh fruit. Industrial processing tomato varieties are preferably of the determinate type. This means that the plants flower at the same time and that the tomatoes are ripe at the same time. Determinate plants have a clearly defined growing cycle of less than 150 days from transplanting the small plants until harvest. This enables harvest of the whole plant at once. The harvesting can be done manually or mechanically. Processing tomato plants used for industrial purposes are preferably grown as a bush on the ground (not as a cordon). Preferably processing tomato varieties produce relatively firm fruits; tomatoes sold directly to end consumers are in general too soft for industrial processing. In general, determinate varieties produce tomatoes that are relatively firm. These tomatoes are firmer due to higher fiber content resulting in a hard compact flesh.

According to the present process the processing tomatoes are allowed to dehydrate while still on the vine and/or they are subjected to a dehydration treatment after harvesting. Dehydration of processing tomatoes, as used in the context of the present invention, is meant to refer to the loss of water from the intact tomatoes, typically by evaporation. As is known by the skilled person, the processing tomato fruit cuticle usually does not contain any stomata, pores or channels. Thus, the natural water-permeability of the skin of processing tomatoes is very low and the fully ripe tomato fruit retains water very well. As a result, ordinary processing tomatoes that are allowed to 'dehydrate' on the vine after fully ripening and/or allowed to 'dehydrate' post-harvesting will not in fact dehydrate, but instead will undergo degradation and start to rot. Hence, it is an essential aspect of the present invention that the cuticle of the tomato is permeable to water. The cuticle of a ripe tomato can be made permeable to water by human interference, e.g. by chemical treatment, using agents such as organic solvents that remove the epicuticular wax layer.

Since the aforementioned methods of making the cuticle water-permeable are typically rather laborious and may have other disadvantages, an especially preferred embodiment of the invention is provided wherein the water-permeability of the tomato skin or cuticle is the result of specific tomato genotype characteristics, such as for example disclosed and explained in WO 01/13708 and WO 2006/030445.

Hence, according to a preferred embodiment of the present invention the tomatoes are characterised by having an endogenous permeability to water, preferably resulting from the development of pores or fissures during ripening. As used herein the term 'endogenous' has the meaning of not being the direct result of any treatment or manipulation of the fruit while growing or during or after ripening. In an even more preferred embodiment, said pores or fissures are the result of spontaneous cracking of the tomato cuticle during the ripening process.

According to a particularly preferred embodiment of the present invention, the tomatoes belong to a variety wherein a polypeptide is expressed having an amino acid sequence according to SEQ ID no. 1, or a functional homologue of said polypeptide. The aforementioned polypeptide is encoded for by the cwp gene (SEQ ID no. 2), as is described in more detail in WO 2006/030445, the expression of which results in increased cuticle water permeability (CWP). It has been hypothesized that the expression of the cwp gene leads to a structurally modified cuticle which undergoes fissuring during fruit expansion due to reduced elasticity.

The term 'functional homologue thereof', as used herein refers to a polypeptide which differs from the naturally occurring polypeptide encoded for by the cwp gene (SEQ ID no. 1 and SEQ ID no. 2 respectively), only by minor modifications, but which maintain the structure and functionality of the naturally occurring form. Such changes include, but are not limited to: changes in one or a few amino acid side chains; changes in one or a few amino acids, including deletions (e.g., a truncated version of the peptide) insertions and/or substitutions; changes in stereochemistry of one or a few atoms; and/or minor derivatizations. As used herein, a homologue has either enhanced or substantially similar functionality as the naturally occurring polypeptide. Typically, when optimally aligned, such as by the programs GAP or BESTFIT using default parameters, the naturally occurring polypeptide and a homologue thereof share at least a certain percentage of sequence identity. GAP uses the Needleman and Wunsch global alignment algorithm to align two sequences over their entire length, maximizing the number of matches and minimizes the number of gaps. Generally, the GAP default parameters are used, with a gap creation penalty=8 and gap extension penalty=2. For proteins the default scoring matrix is Blosum 62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752, USA. Alternatively percent similarity or identity may be determined by searching against databases such as FASTA, BLAST, etc.

A homologue herein is understood to comprise a polypeptide having at least 70%, preferably at least 80%, more preferably at least 90%, still more preferably at least 95%, still more preferably at least 98% and most preferably at least 99% amino acid sequence identity with the naturally occurring polypeptide, mentioned above, expression of which still leads to a structurally modified cuticle which may have reduced cuticle elasticity, such that fissuring occurs during fruit expansion.

The processing tomatoes that are used in accordance with the invention preferably belong to cultivars producing fruits that are, on average, at least 3 cm, preferably 4 cm, most preferably 5 cm in diameter when fully ripe. According to another embodiment of the invention, said processing tomatoes belong to cultivars characterised by producing fruits having an average weight when fully ripe of at least 15 g, preferably at least 30 g, most preferably at least 50 g.

Yet, according to another embodiment of the invention, said processing tomatoes belong to cultivars characterised by producing fruits having an average solids content when fully ripe of less than 12 wt %, preferably of less than 10 wt %, most preferably of less than 8 wt %.

Suitable examples of publicly available introgression lines of *L. esculentum* (nowadays referred to as Solanum lycopersicon) described as having epidermal reticulation (an indicator of cuticle cracking) can be obtained from the Tomato Genetic Resource Centre (TGRC), under the accession numbers LA3935 (line TA517), LA3494 (line IL4-4) and LA3937 (line TA1473).

As mentioned here above, the present process utilises processing tomatoes that have been dehydrated to a Brix value within the range of 5-10. According to a preferred embodiment of the invention a method is provided wherein the tomatoes have been allowed to dehydrate until having a Brix value within the range of 5.5-9.5, preferably within the range of 6-9. The Brix values of the dehydrated processing tomatoes typically refer to average values of batches or lots of processing tomatoes that are dehydrated and processed in accordance with the invention. It will be clear to the skilled person that the Brix value of individual dehydrated fruits may well be outside the recited ranges, as it will depend on a variety of external factors during the ripening as well as during the dehydration process. Hence, embodiments wherein processing tomatoes are employed having deviant Brix values are within the scope of the present invention, provided that a significant fraction, typically at least 10%, preferably at least 25%, more preferably at least 50%, of the dehydrated processing tomatoes has a Brix value within the specified ranges.

Typically, dehydration of the tomato types defined herein before until having a Brix value within the specified ranges, involves removal of between 5-50% of the water originally present in the ripe tomato, preferably of between 7-35%, most preferably 8-25% thereof. Hence, according to a particularly preferred embodiment of the present invention a method is provided wherein the tomatoes have been allowed to dehydrate to such an extent that the total water loss is within said ranges.

The dehydration of the tomato types defined herein before, until having a suitable Brix value in accordance with the invention, is typically accompanied by an average reduction in weight of between 5-50% relative to the weight of the tomato when ripe, preferably of between 10-25%.

As explained herein before, in the present process dehydration of the processing tomatoes may be achieved by leaving the ripe tomato fruit on the vine or by harvesting the fruit and subjecting it to a drying treatment. The harvested tomato fruit may suitably be dehydrated by drying the tomato fruit in an oven, optionally under reduced pressure. It is also feasible to dry the harvested tomato fruit by simple air drying, optionally at elevated temperature.

As mentioned herein before, gamma amino butyric acid (GABA) content was found to increase markedly, i.e. relative to total dry solids during dehydration of the tomatoes. The GABA and glutamate pathways are closely linked. In most cases, GABA is synthesized from glutamate by irreversible action of the enzyme glutamate decarboxylase (GAD), which is present to high levels in tomato. The physiological role of GABA in higher plants has been the subject of much debate. Without wishing to be bound by theory, GABA is hypothesized to be involved in the plant response to stress as it is rapidly produced in large quantities in response to biotic and abiotic stress. Possibly, GABA functions as a signaling molecule to initiate the appropriate cellular response. The stress induced by water loss from the tomato fruit during dehydration may thus directly cause the GABA levels to be increased. Typically, in accordance with the invention, the dehydrated processing tomatoes and the pastes produced there from comprise at least 0.07 wt % of GABA, when corrected to 12 Brix, more preferably at least 0.09 wt %, most preferably at least 0.1 wt %, when corrected to said Brix level. Furthermore, said dehydrated tomatoes and pastes are typically characterised by having a glutamate to GABA ratio of less than 12, preferably less than 9, more preferably less than 7, most preferably less than 6. Typically said ratio is at least, 1, preferably at least 2, most preferably at least 3.

The contents of several other free amino acids found in tomatoes significantly alter as well during dehydration of the tomatoes. Changes in certain amino acid content of tomatoes may typically have a significant impact on the taste of tomatoes and tomato products.

Aspartic acid content of the tomato fruits, i.e. relative to dry solids, typically increases during dehydration of the fruit. Aspartic acid formation is linked closely to glutamate metabolism in accordance with the following equation:

Glutamate+Oxalate→Aspartate+αketoglutarate

Glutamine also was found to usually increase, i.e. relative to total dry solids, during dehydration of the tomatoes. As the metabolism of glutamate and glutamine is tightly linked, it is hypothesized, without wishing to be bound by any theory, that glutamine is formed at the expense of glutamate.

Alanine content of the tomato fruits has also been found to increase during dehydration, possibly as the result of another glutamate reaction:

Glutamate+Pyruvate→Alanine+αketoglutarate.

Hence, the dehydrated processing tomatoes that are processed in accordance with the presence invention, as well as the pastes thus obtained, are typically characterised by having a glutamate to alanine ratio within the range of less than 25, preferably less than 15, more preferably less than 10, most preferably less than 7. Typically said ratio is at least 1, preferably at least 3, most preferably at least 4.

Furthermore, the dehydrated processing tomatoes and tomato pastes of the invention typically have a glutamate to aspartate ratio of less than 3, preferably less than 2.5, more preferably less than 2, most preferably less than 1.7. Typically said ratio is at least 0.5, most preferably at least 1.

Typically said dehydrated processing tomatoes and tomato pastes comprise less than 0.6 wt % of glutamic acid, corrected to 12 Brix, more preferably less than 0.55 wt %, most preferably less than 0.5 wt %, corrected to said Brix level. Typically said dehydrated tomatoes comprise at least 0.05 wt % of alanine, corrected to 12 Brix, more preferably at least 0.075 wt %, most preferably at least 0.09 wt %, corrected to said Brix level. Typically said tomatoes comprise at least 0.07 wt % of GABA, corrected to 12 Brix, more preferably at least 0.09 wt %, most preferably at least 0.1 wt %, corrected to said Brix level.

Typically, the total sugar content of the processing tomatoes, in accordance with the invention, was found to increase slightly during dehydration of the tomatoes. Sucrose content was found to increase most significantly, whereas the percentage of increase of glucose and fructose is relatively small. Sugars are formed during degradation of starch as part of the ripening process and usually reach a peak when the tomato is fully ripe. In red-fruited tomato species, sucrose does not accumulate in the fruit but is hydrolysed to glucose and fructose by invertases to fulfill energy requirements, as part of respiration. Glucose and fructose therefore normally make up about 22% and 25% respectively of ripe tomato fruit dry matter, whereas sucrose is only present in ripe tomatoes in amounts of approximately 1%, based on the dry weight. Without wishing to be bound by theory, it is hypothesized that the increase in sucrose during dehydration on the vine results from the inhibition of sucrose breakdown to glucose and fructose as a result of reduced cellular respiration. Reduced respiration occurs naturally as either part of the senescence process or as a stress response, e.g. in response to water loss from the fruit.

Hence, in a preferred embodiment the dehydrated processing tomatoes and the pastes obtained in accordance with the invention, are characterized by having an increased sucrose content, and by having an increased ratio of sucrose to fructose and/or glucose. Typically the dehydrated tomatoes and the tomato pastes comprise at least 0.4 wt % of sucrose, when corrected to 12 Brix, more preferably at least 0.45 wt %, most preferably at least 0.5 wt %, when corrected to said Brix level. Typically the ratio of the amount of the total amount of fructose and glucose to the amount of sucrose in said dehydrated tomatoes and tomato pastes is less than 40, more preferably less than 30, most preferably less than 25. Since sucrose is much more effective in imparting sweet taste than glucose, the changes that were found in are quite significant from an organoleptic point of view.

The major organic acid components of tomato fruit are malic acid and citric acid. Typically, the malic acid content of the dehydrated processing tomatoes and the tomato pastes of the invention, is slightly decreased, compared to conventional tomato fruit and products produced there from. Citric acid content was found typically to decrease during dehydration of the tomatoes while still attached to the vine. In line with this decrease, the pH of the tomatoes and tomato pastes was found usually to increase.

Hence, the dehydrated processing tomatoes as well as the pastes obtained in accordance with the invention, are typically characterised by having decreased citric acid content, as compared to conventional tomatoes and pastes. Typically, citric acid is comprised in the dehydrated tomatoes and pastes in amounts of below 0.6 wt %, when corrected to 12 Brix, preferably of below 0.55 wt % when corrected to said Brix level. Typically, the ratio of the amount of sucrose to the amount of citric acid in the dehydrated tomatoes and pastes of the invention is higher than 0.2, preferably higher than 0.4, most preferably said ratio is higher than 0.5.

Typically, the decrease of citric acid and glutamic acid levels during dehydration affect the normal fresh tomato taste and flavour of the dehydrated processing tomatoes and pastes obtained there from. Such effects of dehydration on organoleptic properties, especially taste and/or flavour, can be evaluated by tasting of the tomatoes and/or paste by one or more test subjects and comparing it with a control. It is to be noted that these effects are more pronounced at relatively high Brix levels, e.g. at a level of approximately 12 instead of a Brix level of around 7, which is the more common level for a typical product containing the tomato paste of the invention.

The present process comprises harvesting the processing tomatoes either when completely or partly dehydrated or before dehydration, which may include any process or method commonly used for harvesting normal ripened processing tomatoes. Usually, but not necessarily, the harvested tomatoes will be transported to a large processing facility, where they are collected and where they may subsequently be washed, typically using chlorinated water and rinsed using tap water, stored and subsequently sorted and/or selected, in order to remove those tomatoes that present an inadequate ripening degree, an intensive contamination by molds or insects and physical damage. As will be clear to the skilled person these operations per se are known and common in the field of tomato processing and any adjustments to the method can be made in this regard without departing from the scope of the invention.

In accordance with the present invention the harvested and dehydrated processing tomatoes are comminuted or macerated, which is meant to include any process that can be employed to disintegrate or break the tomatoes, typically, in order to obtain a pumpable mass, also referred to as juice or pulp. Typically the comminuting or macerating is continued until particle size in the pumpable mass is reduced to the desired dimensions. Any type of operation and/or apparatus know to or conceivable for the skilled person may be used in accordance with the invention. According to a preferred embodiment a chopper pump is employed, wherein the tomatoes are pressed through square holes, typically 1-2 cm in diameter.

According to a particularly preferred embodiment of the invention, a method is provided wherein the pumpable mass obtained by comminuting or macerating the dehydrated processing tomatoes is sieved, in order to remove seeds and/or skin. In conventional tomato processing plants, screens are used for this purpose having a mesh size ranging from 0.5-2 mm. Although any type of screen may be used without departing from the scope of the invention, a particular advantage of the present invention resides in the possibility of employing this conventional equipment when processing the afore defined dehydrated tomatoes, without problems relating to fouling up of the screens, as a result of the increased solids content after dehydration of the tomatoes. Hence, according to a preferred embodiment of the present method, the comminuted or macerated tomatoes are sieved using a screen having a mesh size within the range of 0.5-2 mm. It is observed that the screen size affects the viscosity, the coarseness and the colour of the obtained paste, wherein the viscosity and coarseness increase with increasing mesh size and the colour becomes less appreciable with increasing mesh size. It is within the skills of the trained professional to design the most appropriate sieving operation, depending on the desired characteristics of the obtained product In another preferred embodiment of the invention, a method is provided as described herein before, comprising the additional step of so-called breaking of the comminuted or macerated tomatoes which aims at inactivating enzymes released during comminuting and/or macerating of the dehydrated processing tomatoes, which enzymes affect the flavour and/or rheological properties of the pulp or juice and consequently that of the end-product obtained. Especially the enzymes pectin methyl esterase (PME) and poly galacturonase (PG) play a critical role in these processes, both these enzymes catalyzing reactions that result in weakening of the entangled networks of cell-wall-bound polymers like pectins. Pectin is formed between the microscopic cells, which make up the fleshy red tissues, cementing these together. The more pectin is retained, the thicker the final product; thus it is a great concern in the manufacture of "thick" products such as ketchup. The breakdown of these polymers, which is also part of the natural ripening process, results in the formation of individual polymer components like galacturonic acids, which give a more fruity and acid taste to the tomatoes. Both cold-breaking and hot-breaking methods are known in the art and any of the known processes may be employed in accordance with the invention. Typically the breaking operation comprises heating to a temperature of between 55-80° C. (cold break) in order to obtain products characterised by having a flavour described as fresh and fruity, to a temperature of between 80-100° C. (hot break) in order to obtain products characterised by having a flavour described as cooked and savoury. It is also known to employ temperature of below 55° C. or above 100° C. (super hot break). Besides the rheology and flavour, the break temperature is also observed to affect the coarseness and the colour of the obtained product, wherein the coarseness increase with increasing temperatures and the colour becomes less appreciable with increasing temperatures. It is within the skills of the trained professional to design the most appropriate breaking operation, depending on the desired characteristics of the obtained product. In a preferred embodiment, the breaking operation comprises heating of the pumpable juice or pulp in a forced-recirculation heater, a single pass heat exchanger or a serpentine heater.

In another equally, preferred embodiment the pumpable juice or pulp, obtained by comminuting or macerating the dehydrated processing tomatoes, optionally followed by any of the above mentioned operations, is concentrated by removal of water, such as to reduce packaging storage and transport costs, minimize browning and/or to maximize factory throughput. Typically the concentration step is performed by evaporation by heating, usually but not necessarily under reduced pressure, although entirely different techniques are available. As will be understood by the skilled person, applying reduced pressure can suitably reduce thermal damage to the product, thus improving the quality of the obtained product. Preferably the concentration is performed using a so-called forced reticulation multiple effect counter current evaporator. In this document the term 'paste' is typically used to denote the product that is obtained after concentration of the pumpable juice or pulp. The heat applied and the evaporation of water greatly affect the flavour of the obtained paste, such that depending on the heat intensity and the amount of water removed, products can be obtained ranging in flavour characteristics from "green", "fruity/sulphury", to "caramelic" or even "burnt". It is within the skills of the trained professional to design a concentration process in such a way that the most suitable product in terms of both Brix value and flavour characteristics is obtained.

As is common in the field of producing processed tomato products, the paste obtained in accordance with the present method, may be packaged and stored to enable the production of finished products out of season.

As mentioned before, it was found that the rheological properties of pastes produced in accordance with the invention do not deteriorate as the period of dehydration post ripening increases up to the time the processing tomatoes have a Brix value of 10. More in particular it was found that consistency and viscosity of pastes produced in accordance with the invention do not differ significantly from that of standard tomato pastes, i.e. produced from tomatoes of the same variety that were harvested when ripe and that were not subjected to post-harvesting dehydration operations. Typical rheology parameters are "viscosity" and/or "consistency", which refer to the resistance to change in form exhibited by the tomato pastes. "Viscosity" or "consistency" reflect the flow characteristics of the paste as well as the degree of separation of free liquid from the solids. The viscosity or consistency of tomato products is known to be affected by the degree of concentration of the tomato paste, the amount of and extent of degradation of pectin, the size, shape and quality of the pulp, and probably to a lesser extent, by the proteins, sugars and other soluble constituents.

A common value used to express the rheological properties of tomato pastes is the Bostwick value which is determined using instruments such as a Bostwick Consistometer, which measures a flow property of a viscous tomato product. The operational aspects of the Bostwick consistometer may be determined as follows. The paste is placed in the Bostwick Consistometer. The Bostwick Consistometer must be at room temperature (25° C.) and be clean and dry. It must be leveled. A small carpenter's level works well. The paste is diluted to 12 Brix and mixed until there are no visible lumps of tomato puree and/or paste. The chamber is filled; the excess material is scraped off of the top of the chamber with a straight edge. The gate is released and the distance the tomato paste has traveled in cm in 30 seconds is recorded. The paste will have moved to a distance corresponding to its viscosity; the higher the viscosity, the less distance the paste will move. Higher consistency in processed tomato products is perceived to represent better quality. In the processing of such tomato-based products it is recognized that product consistency is dependent upon the presence of pectic substances in the tomatoes, and may be controlled to some extent by the method of manufacture of the tomato based products.

Typically, in accordance with the present invention the Bostwick value of the tomato paste is not more than 13 cm, preferably not more than 12 cm at 12 Brix. Particularly satisfactory Bostwick values in accordance with the invention are within the range of 3-8 cm at 12 Brix, more preferably within the range of 3.5-7 cm and most preferably within the range of 3.5-6.5 cm at said Brix level for pastes produced in accordance with the invention using the hot-break process. For pastes produced using cold break processing the Bostwick value at 12 Brix will be somewhat higher, typically 7-12 cm, preferably 7.5-11, most preferably 8-10 cm when measured in accordance with the above described method. Typically, the Bostwick value of a product produced in accordance with the invention is not more than 120% of that of a paste produced from tomatoes of the same variety that have not been dehydrated, preferably not more than 110%, most preferably not more than 105%.

The yield point expressed in Pa is another parameter that is commonly used for characterising the rheological property of a viscous material. The flow of a viscous material can be determined in relation to shear stress and shear rate. The "yield point" is the amount of shearing stress that must be applied before a material will begin to flow and can be determined from a rheogram (apparent viscosity vs. shear stress data). At stresses larger than the yield point the rate of flow is approximately linear with the shear stress. A generally known method of determining yield points employs a Physica rheometer with a vane spindle under the following conditions. Paste samples are standardised to 12 Brix before testing and are allowed to reach room temp. The Physica rheometer and water bath heating system are switched on 30 minutes before use to allow the sample chamber to stabilise at the testing temperature (25° C.). Tomato paste to be tested is then placed in the chamber such that it completely fills the chamber. The vane spindle is lowered into the paste. The stress test is performed by increasing shear stress and taking measurement points every 5 seconds for a total of 60 measurement points (i.e. 300 seconds, 5 mins.). The data is analysed using a Herschel-Bulkley method to determine the yield point in Pa for the pastes.

Typically the tomato pastes of the present invention have a yield point at 12 Brix within the range of 20-75 Pa, preferably within the range of 25-60 Pa, most preferably within the range of 30-55 Pa. It is furthermore preferred that the yield point of a product produced in accordance with the invention does not differ from that of a control paste produced from tomatoes of the same variety that have not been dehydrated, by more than 20%, preferably not more than 15%, most preferably not more than 10%.

In another aspect of the present invention, a method is provided for producing edible processed tomato products comprising mixing a tomato paste obtainable by the process described herein before, with one or more other food ingredients, typically in such amounts that the edible processed tomato product comprises at least 10 wt %, based on dry solids weight, of constituents of the tomatoes.

An "edible processed tomato product" in accordance with the present invention refers to a food or beverage product comprising as one of its components a mixture of soluble and/or insoluble natural tomato constituents, typically a product containing a fraction of whole tomato fruits, admixed with other ingredients. Said product may be liquid semi-solid or solid in accordance with the invention. The adjective "processed" is used herein to preclude tomato fruits as such which are harvested and offered to consumers without any further operation significantly altering the physical state of the fruit. Furthermore the adjective "edible" is used herein specifically to indicate that the product must be suitable for oral consumption and ingestion by a human or an animal, especially a human.

Typical examples of edible processed tomato products in accordance with the invention include passata, pasta sauce, pizza topping, tomato ketchup, salsa, etc. According to a particularly preferred embodiment of the invention, the edible processed tomato product is selected from the group of passata, pasta sauce, pizza topping, ketchup, tomato sauce, tomato soup, tomato puree, tomato paste, tomato juice, tomato powder, tomato dice, crushed tomato, chopped tomato paste and tomato concentrate.

As is known by the skilled person, food ingredients usually employed for producing any of the aforementioned processed tomato products, typically include, sugars, salt, spices, herbs, other vegetable materials, thickeners, stabilising agents, preservatives, etc. In accordance with the invention, the edible processed tomato product preferably comprises at least 10 wt %, based on dry solids weight, of constituents of the tomatoes, as this amount typically allows for the favourable taste characteristic to be attained. Preferably, the product comprises at least 20 wt %, more preferably at least 30 wt. % and most preferably at least 40 wt. %, based on dry solids weight, of constituents of the tomatoes that have been allowed to dehydrate in accordance with the present invention.

Preferably, the method of the present invention does not comprise fermentation of the processed tomato product and/or any of the intermediate products mentioned herein before, e.g. by lactic acid bacteria. It is also particularly preferred that the method does not comprise the addition of lactic acid bacteria in amounts exceeding 0.1 wt. % to the processed tomato products and/or any of the intermediate products mentioned here before. More preferably, the method does not comprise the addition of lactic acid bacteria to the processed tomato products and/or any of the intermediate products mentioned here before.

Typically, according to the present invention, a method is provided further comprising the step of packaging the edible processed tomato product in a sealable container. As will be understood by the skilled person the edible processed tomato product may include the pumpable tomato juice or pulp, optionally after sieving, the concentrated tomato paste, or a finished consumer product including other ingredients, as all described herein before. Hence, the sealable containers can be anything ranging from cans, tins, cartons, jars and the like in relation to finished products to barrels, vessels and the like for storage of juices, pulps or pastes for further industrial processing out of season.

The present method may furthermore include the step of pasteurization or sterilization at any of the afore-described stages of processing. Preferably the present method comprises the step of pasteurizing. According to one preferred embodiment of the present method, the paste obtained after concentration is pasteurized before mixing with other food ingredients and before, during or after packaging, such that it can be stored for out-of-season production of finished products. Alternatively, the processed tomato product may be pasteurized or sterilized after mixing with other food ingredients, most preferably after packaging such that that packaging itself need not be performed under aseptic conditions. For pasteurizing and/or sterilizing any process known to or conceivable for the skilled person may be employed.

Another aspect of the invention relates to an edible processed tomato product that is obtainable by the method as described herein before, especially by the preferred embodiments thereof. Typically, such edible processed tomato products are characterised by comprising at least 1 wt %, more preferably at least 5 wt %, still more preferably at least 10 wt %, most preferably at least 20 wt %, based on dry solids weight, of constituents of processing tomatoes, said constituents being characterised by the expression of the CWP gene sequence or a functional homologue thereof.

According to a preferred embodiment, said processed tomato product is further characterised by having the aforementioned characteristic amino acids, sugars and organic acids contents.

As will be clear from what has been explained herein before, the products made from tomato fruits that have been allowed to dehydrate, have been found to have high levels of GABA as well as very satisfactory rheological properties.

Hence, another aspect of the invention provides a method of increasing the gamma-aminobutyric acid content of a food product or beverage, comprising incorporating in said food product an edible processed tomato product obtainable by the method defined in herein before. Preferably said processed tomato product is incorporated in an amount of at least 1 wt % based on total weight of the food product or beverage, as mentioned herein before, more preferably in an amount of at least 5 wt %, still more preferably at least 10 wt %, most preferably at least 20 wt %.

EXAMPLES

Example 1

Production of Paste from Vine Dehydrated Tomatoes

Growing of the Tomato Lines Trialled

Three publicly available introgression lines described as having epidermal reticulation were obtained from the Tomato Genetic Resource Centre (TGRC) and were trialled in the field in Brazil in 2005, i.e. LA3935; LA3494; and LA3937. The control to be grown alongside these above lines was chosen as E6203 (FM6203) because this was the genetic background for two of the introgression lines. A germination trial in February 2005 enabled percentage germination to be established for each line. A molecular screen confirmed that all plants in the germination trial (a representative sample) contained the introgression and that no out-crossing had taken place.

Seed were sown for transplants on 18 Mar. 2005 and transplants were subsequently planted in the field on $21^{st}$ April.

Material was grown under drip irrigation. Water was reduced approximately 1 month before the usual date of harvest to just 10-15% of the original water supply.

pH and Brix values were monitored from ripening using a selection of fruit from different plants of each line by weekly random sampling of each line throughout the field, homogenising, removal of seeds and measuring Brix with a refractometer. This was repeated at intervals until all fruit at all stages of dehydration were harvested.

Harvesting

Harvesting occurred at three different stages for each line at the required Brix:
Stage 1: 4.5-5° Brix (fruit would normally be harvested at this stage).
Stage 2: 5.5-6° Brix
Stage 3: 6.5-7° Brix Harvesting was manual. Plants were shaken and sorted and fruit was sent to a pilot plant. At the sorting stage, green fruit, discoloured fruit and losses due to mould were recorded.

Processing

Fruit was processed in a pilot plant facility. Each trial followed the same procedure. 70 kg of red fruit entered the pilot plant and was chopped. After chopping the pulp passed through the Break system. The Break system was a Shell-in-Tube heat exchanger in which the tomatoes are brought to a certain temperature, breaking down the enzymes of the tomatoes responsible for pectin degradation. All varieties at the 3 concentration levels had a Hot-Break treatment (the pulp is heated to 90° C. and when the temperature is reached the pulp is circulated at this temperature for 5 minutes). After the Break, the pulp passed through a 1.6 mm sized screen.

The juice that passed through the screen was collected in a tank. Approximately 10 liters of juice from the tank was sucked by vacuum into the evaporator. The product in the evaporator circulated from a heat exchanger, where it was brought to ±70° C., to the vacuum chamber. Fresh juice from the tank was added to the evaporator to maintain the volume of ±10 liters. When 16° Brix was reached, the vacuum in the evaporator was brought to atmospheric pressure. The paste was heated to 90° C. and the evaporator emptied into a bucket. From the bucket the paste was manually put into cans and seemed. The cans were then put into boiling water for 10 minutes to pasteurise the paste. The procedure for the evaporation, filling and pasteurisation described above is in accordance with the conventional procedures used.

Observations

All vine concentrating lines showed an increase in Brix relative to the controls and LA3935 showed the highest rate of Brix increase. Fruit dehydrated more slowly in the field compared to greenhouse conditions and therefore maximum Brix potential could not be reached. Despite this, line LA3935 reached 7° Brix at stage 3, before weather conditions prevented further fruit harvests.

Analysis

Approximately 1 kg of extra fruit was taken from each trial for bench-top analysis. Fruit were quartered and then homogenised in a blender before being sieved to remove seeds and skins. Bench-top analysis was then performed using standard protocols for Brix, titratable acidity, pH, Bostwick, colour and total solids. Brix and pH measurements were also taken from juice from the pilot plant because there are often differences between the two measurements.

Cans of paste produced from on-vine-dehydrating fruit and controls, as described in example 1, were opened and re-measured for Brix and pH. Pastes were then corrected to 12° Brix (for ease of comparison), divided into separate jars and vials and frozen. The paste was then analysed using standard laboratory techniques. All pastes were analysed for the following taste compounds:
Sugars: glucose, fructose, sucrose
Organic acids: citric acid, malic acid
Free Amino acids: 22 in total.

In addition, a trained taste panel of 10 people evaluated pastes produced at each stage of dehydration, relative to the control. Pastes were all evaluated at 10° Brix. Pastes were evaluated for colour, tomato aroma, fresh tomato aroma, acid aroma, tomato taste, fresh tomato taste, acid taste, sweet taste and graininess in the mouth.

The effect of on-vine-dehydration on Bostwick values of pastes produced from the LA3494 tomatoes was also assessed.

Analysis of Paste Components

Pastes were corrected to 12° Bx and analysed using standard analytical techniques. There were differences between vine concentrating fruit pastes and controls. Changes in amino acid compositions of the pastes are summarised in table 1 below.

The largest increase in GABA was seen between stage 1 and 2 of line LA3937 (2-4× increase). Large increases were also seen between stage 2 and 3 for LA3935 (~3×).

The glutamic acid content decreases in pastes produced from vine concentrating fruit, although the extent of the decrease appears to be line-dependent and stage-dependent.

Aspartic acid increases with vine concentration, with LA3494 showing the largest increase at 60%.

Glutamine also was found to increase in pastes made from fruit that have been left to vine concentrate, with the greatest increases seen in line LA3935 between stage 1-2. Alanine also shows large increases with vine concentration (2-3× for all lines). Again, LA3937 shows the largest increase.

TABLE 1

Results of free amino acid analysis of vine dehydration.

| Amino Acid | Changes in paste as a result of vine dehydration relative to controls (non-vine-concentrated) (+ increase, − decrease, = equal) | |
|---|---|---|
| Aspartic acid | + | major |
| Threonine | = | |
| Serine | + | major |
| Asparagine | + | minor |
| Glutamic acid | − | major |
| Glutamine | + | major |
| Proline | = | |
| Glycine | + | |
| Alanine | + | major |
| Valine | + | |
| Cystine | | N.A. |
| Methionine | = | |
| Isoleucine | + | |
| Leucine | + | |
| Tyrosine | + | |
| Phenylalanine | = | |
| γ-Aminobutyric acid (GABA) | + | major |
| Ethanolamine | = | |
| Lysine | = | |
| Histidine | = | |
| Tryptophan | | N.A. |
| Arginine | = | |

The total sugar content increases with dehydration. Sucrose content shows the largest percentage increase in all vine dehydrating varieties (up to 3×), whereas % increases in glucose and fructose are relatively small. The largest increases in sugar are between stages 1-2, compared to 2-3, although only LA3935 pastes at stage 2-3 were analysed.

There is a slight decrease in paste malic acid levels as fruit vine dehydrate but this is relatively minor. However, citric acid decreases between 10-40% from stage 1 to 3, depending on the variety tested. In line with the large decrease in citric acid, the pH of the paste increases and there is a decrease in titratable acidity. LA3935 paste shows the greatest decrease in citric acid between stage 1 to 2, as opposed to between stage 2 to 3. Interestingly this does not correspond to the largest increase in Brix (0.22° Bx between stage 1-2 compared to 0.72° Bx between stage 2-3), the largest increase in pH (0.77 units between stage 1-2 compared to 0.19 units between stage 2-3) or the largest decrease in titratable acidity (0.11% compared to 0.16%).

Sensorial Analysis of Paste

When pastes were tested sensorially by a trained panel using a ranking test (R. M. Pangborn. 1984. "Sensory techniques of food analysis", D. W. Gruenwedel and J. R. Whitaker, eds, in *Food Analysis. Principles and Techniques*, Vol. 1, New York: Marcel Dekker, p. 59), there were no negative taste or texture attributes reported for pastes made from fruit that had been left on the vine for extended periods. Furthermore, the panel reported an increase in the perception of sweetness of pastes produced from vine-dehydrated fruit and a reduction in acid taste. This may be due to the increased levels of sucrose, the decrease in glutamate (which would mask sweetness), and/or the decrease in the levels of citric acid and other organic acids.

This finding is significant because one of the most common complaints of tomato-based products is that they are too acidic. It is concluded that paste from vine-dehydrated fruit could be used to produce products requiring the addition of less sugar.

Bostwick Analysis of Paste

LA 3494 pastes and LA 3935 pastes, produced from fruit that had been left on the vine for extended periods to reach 6-7 Brix relative to paste produced from fruit at "normal" harvest date (approx 4.5-5 Brix), were tested for consistency using a Bostwick Consistometer in accordance with the protocol described herein. All pastes were tested at 12 Brix. The LA3494 stage 1 paste was found to have a Bostwick of 4.75 cm, and the stage 2 paste had a Bostwick of 4.75 cm. The LA3935 stage 1 paste was found to have a Bostwick of 6 cm and the stage 3 paste also had a Bostwick of 6. It is therefore concluded that the on-vine-dehydration of the LA3494 and LA3935 tomatoes does not affect the consistency of the pastes produced there from.

Viscosity Analysis of Paste

The pastes produced from the LA 3494 and LA 3935 fruit that had been left on the vine for extended periods to reach 6-7 Brix relative to paste produced from fruit at "normal" harvest date (approx 4.5-5 Brix), were tested for viscosity using a Physica rheometer with a vane spindle under the following conditions. Paste samples were standardised to 12 Brix before testing and were allowed to reach room temp. The Physica rheometer and water bath heating system were switched on 30 mins. before use to allow the sample chamber to stabilise at the testing temperature (25 C). Tomato paste to be tested was then placed in the chamber such that it completely filled the chamber. The vane spindle was then lowered into the paste. The stress test was performed by increasing shear stress and taking measurement points every 5 seconds for a total of 60 measurement points (i.e. 300 seconds, 5 mins.). Measurements were performed in triplicate. The data was analysed using a Herschel-Bulkley method to determine the yield point in Pa for the pastes. The LA3935 stage 1 had a yield point of 36.97 Pa (SD 2.84) and LA3935 stage 3 had a yield point of 40.93 (SD 2.54). LA3494 had a yield point of 54.93 (SD 3.73) at stage 1 and 57.97 (SD 5.39) at stage 2. These values were thus all well within the ranges that are generally considered as acceptable for tomato pastes to be incorporated into food products. Moreover, these results indicate that the dehydration does not result in a significant deterioration of the rheologic properties of the paste, as would have been expected.

Example 2

In another trial, the following year, introgression lines LA3935 and LA3494 and a control, E6203, where grown under similar conditions as described in example 1. For the production of pastes from stove-dehydrated tomatoes, fruits were harvested (stage 1) washed, selected, separated and weighted. Fractions of the stage 1 tomatoes of each line were separated, packed and frozen at −18° C. Further fractions of each of the introgression lines, consisting of 1000 stage 1 tomatoes were placed in a stove operated at a constant temperature of approximately 30° C. Calcium Chloride was added in the stove to remove the humidity. All the tomatoes placed in the stove were weighed every 2 days. As the calculated brix reached the desired value, the tomatoes were removed from the stove and stored in the freezer at −18° C. until all tomatoes achieved the desired stage. After that, all tomatoes were defrosted to ambient temperature and processed in the kitchen simulating the tomato process. Table 2a shows the batches of non-dehydrated and stove-dehydrated tomato fruits were used for producing pastes.

TABLE 2a non-dehydrated and stove-dehydrated tomato fruit batches that were used for producing pastes.

| E6203 | LA 3494 | LA 3935 |
|---|---|---|
| Stage 1: 5° Brix | Stage 1: 4.5°-5°Brix | Stage 1: 4.5-5°Brix |
| | Stage 2: 7° Brix (6-8° Brix) | Stage 2: 7° Brix (6-8° Brix) |
| | Stage 3: 10° Brix (9-11° Brix) | Stage 3: 10° Brix (9-11° Brix) |
| | Stage 4: 14° Brix (13-15° Brix) | Stage 4: 14° Brix (13-15° Brix) |

In addition, during the same field trial, batches of tomatoes were harvested post ripening at different stages, washed, selected, separated weighed and stored in the freezer at −18° C. until use. For producing the pastes, all tomatoes were defrosted to ambient temperature and processed in the kitchen simulating the tomato process. Table 2b shows the batches of non-dehydrated and vine-dehydrated tomato fruits used for producing pastes.

TABLE 2b non-dehydrated and vine-dehydrated tomato fruit batches that were used for producing pastes.

| E6203 | LA 3494 | LA 3935 |
|---|---|---|
| Stage 1: 5° Brix | Stage 1: 4.5-5° Brix | Stage 1: 4.5-5° Brix |
| | Stage 2: 6° Brix | Stage 2: 6° Brix |
| | Stage 3: 7° Brix | Stage 3: 7° Brix |

They were processed in the same way as the stove products. For all pastes concentration was conducted at boiling temperature until 7° Brix.

Table 2c recites the measured Brix values, pH and citric acid levels of the non-dehydrated and the stove or vine-dehydrated tomatoes.

TABLE 2c

Brix values, pH and citric acid levels of the non-dehydrated and the stove or vine-dehydrated tomatoes.

| Variety | Starting Brix | Brix Achieved | pH | Final Paste Brix | % of Citric Acid |
|---|---|---|---|---|---|
| Stove-dehydrated samples | | | | | |
| 1 | 3935 | 4.30 | 12.84 | 4.50 | 7.32 | 0.41 |
| 2 | 3935 | 4.10 | 8.64 | 4.53 | 7.45 | 0.38 |
| 3 | 3935 | 4.20 | 6.17 | 4.49 | 7.47 | 0.41 |
| 4 | 3935 | 4.40 | 4.40 | 4.20 | 7.40 | 0.57 |
| 5 | 3494 | 4.50 | 12.40 | 4.54 | 7.12 | 0.36 |
| 6 | 3494 | 4.30 | 8.60 | 4.56 | 7.63 | 0.37 |
| 7 | 3494 | 4.30 | 6.02 | 4.60 | 6.86 | 0.34 |
| 8 | 3494 | 4.20 | 4.20 | 4.21 | 7.24 | 0.61 |
| 9 | 6203 | 4.20 | 4.20 | 4.20 | 7.65 | 0.62 |
| Field-dehydrated samples | | | | | |
| 10 | 3935 | — | 7.03 | 4.70 | 6.82 | 0.25 |
| 11 | 3935 | — | 6.51 | 4.57 | 6.73 | 0.30 |
| 12 | 3535 | — | 4.95 | 4.49 | 6.91 | 0.33 |
| 13 | 3494 | — | 6.68 | 4.51 | 7.23 | 0.33 |
| 14 | 3494 | — | 5.88 | 4.43 | 7.40 | 0.36 |
| 15 | 3494 | — | 5.01 | 4.31 | 7.18 | 0.24 |
| 16 | 6203 | — | 4.50 | 4.42 | 7.41 | 0.42 |

The GABA and glutamic acid levels of the pastes were also determined. These levels, corrected to 12 Brix, are shown in table 2d.

TABLE 2d

GABA, glutamic acid, glutamine and alanine levels (all in g/kg) of the pastes produced from of the non-dehydrated and the stove or vine-dehydrated tomatoes.

| Variety | Starting Brix | Brix after Stove/field dehydration | Glutamic Acid at 12 Bx | GABA at 12 Bx | Glutamine at 12 Bx | Alanine (12 Bx) |
|---|---|---|---|---|---|---|
| Stove | | | | | | |
| 1 | 3935 | 4.30 | 12.84 | 6.41 | 1.18 | 0.39 | 1.18 |
| 2 | 3935 | 4.10 | 8.64 | 6.59 | 0.95 | 0.53 | 1.29 |
| 3 | 3935 | 4.20 | 6.17 | 7.60 | 0.79 | 0.64 | 1.19 |
| 4 | 3935 | 4.40 | 4.40 | 5.38 | 0.49 | 0.45 | 0.19 |
| 5 | 3494 | 4.50 | 12.40 | 6.93 | 1.53 | 0.71 | 6.93 |
| 6 | 3494 | 4.30 | 8.60 | 7.16 | 1.34 | 0.57 | 7.16 |
| 7 | 3494 | 4.30 | 6.02 | 6.21 | 1.31 | 0.84 | 6.21 |
| 8 | 3494 | 4.20 | 4.20 | 5.93 | 0.78 | 0.46 | 5.93 |
| 9 | 6203 | 4.20 | 4.20 | 6.62 | 0.83 | 0.41 | 6.62 |
| Field | | | | | | |
| 10 | 3935 | — | 7.03 | 4.15 | 1.43 | 0.49 | 4.15 |
| 11 | 3935 | — | 6.51 | 4.08 | 0.87 | 0.59 | 4.08 |
| 12 | 3535 | — | 4.95 | 3.04 | 0.45 | 0.61 | 3.04 |
| 13 | 3494 | — | 6.68 | 2.95 | 1.11 | 0.32 | 2.95 |
| 14 | 3494 | — | 5.88 | 3.29 | 0.91 | 0.39 | 3.29 |
| 15 | 3494 | — | 5.01 | 3.53 | 0.57 | 0.53 | 3.53 |
| 16 | 6203 | — | 4.50 | 3.11 | 0.70 | 0.86 | 3.11 |

Sensorial Test Using Quantitative Descriptive Analysis®

In addition to the sensorial test using ranking (see above), pastes produced from field-grown LA3935 and LA3494 tomatoes were tested and compared for sensorial characteristics by a panel of 10 trained flavourists with high sensory acuity using the internationally recognized method of QDA® (Quantitative Descriptive Analysis) (Manual on Descriptive Analysis Testing (1992). Robert C. Hootman, Editor. ASTM Manual Series: MNL 13. Chapter 2, pp 15-21). Samples were diluted to 10° Brix and served at 65° C., without carrier. Results were conclusive, significant and consistently showed that for both varieties the intensity of tomato sensory attributes (including sweetness) increased in paste produced from fruit that had been left on the vine to dehydrate to 6.5 to 7° Brix, relative to paste of the same variety that had been harvested at normal harvest date i.e. without dehydration at 4.5-5° Brix. The only exception with respect to increase in intensity of tomato sensory attributes was that of acidity, which decreased markedly in paste of both varieties produced from fruit that had been left to dehydrate on the vine to 6.5 to 7° Brix, even in samples where pH was very similar at the two different stages of harvest.

---

The invention claimed is:

1. A method of producing a tomato paste comprising comminuting or macerating dehydrated processing tomatoes that express the cwp gene (SEQ ID NO: 2), wherein at least 50% of the dehydrated processing tomatoes have been dehydrated on the vine prior to said comminuting and macerating to a Brix value in the range of 6-9 and said dehydrated tomatoes have a citric acid content below 0.6 weight % when corrected to 12 degrees Brix; and wherein the tomato paste comprises at least 0.09 weight % of GABA when corrected to 12 degrees Brix.

2. The method of claim 1, wherein the tomato paste comprises at least 0.10 wt % of GABA when corrected to 12 degrees Brix.

3. The method of claim 1, wherein the tomato paste has a ratio of the amount of sucrose to the amount of citric acid of higher than 0.4.

4. The method of claim 1, further comprising heating the comminuted or macerated tomatoes to inactivate the cell wall degrading enzymes and/or to remove water.

5. A method for increasing the gamma-aminobutyric acid content of a food product or beverage, comprising incorporating into said food product or beverage the tomato paste of claim 1.

6. The method of claim 1, wherein the tomato paste has a ratio of the amount of sucrose to the amount of citric acid of higher than 0.2.

7. The method of claim 1, wherein the ratio of the total amount of fructose and glucose to the amount of sucrose in said dehydrated tomatoes is less than 40.

8. A method of producing a tomato paste comprising comminuting or macerating dehydrated processing tomatoes that express a polypeptide having an amino acid sequence of SEQ ID NO: 1 or a polypeptide having at least 95% identity of SEQ ID NO: 1 wherein at least 50% of the dehydrated processing tomatoes have been dehydrated on the vine prior to said comminuting and macerating to a Brix value in the range of 6-9 and said dehydrated tomatoes have a citric acid content below 0.6 weight % when corrected to 12 degrees Brix; and wherein the tomato paste comprises at least 0.09 weight % of GABA when corrected to 12 degrees Brix.

9. The method of claim 8, wherein dehydrated processing tomatoes express a polypeptide having the amino acid sequence of SEQ ID NO: 1.

10. The method of claim 8, wherein the tomato paste comprises at least 0.10 wt % of GABA when corrected to 12 degrees Brix.

11. The method of claim 8, wherein the tomato paste has a ratio of the amount of sucrose to the amount of citric acid of higher than 0.4.

12. The method of claim 8, further comprising heating the comminuted or macerated tomatoes to inactivate the cell wall degrading enzymes and/or to remove water.

13. A method for increasing the gamma-aminobutyric acid content of a food product or beverage, comprising incorporating into said food product or beverage the tomato paste of claim 8.

14. The method of claim 9, wherein the tomato paste comprises at least 0.10 wt % of GABA when corrected to 12 degrees Brix.

15. The method of claim 9, wherein the tomato paste has a ratio of the amount of sucrose to the amount of citric acid of higher than 0.4.

16. The method of claim 8, wherein the tomato paste has a ratio of the amount of sucrose to the amount of citric acid of higher than 0.2.

17. The method of claim 8, wherein the ratio of the total amount of fructose and glucose to the amount of sucrose in said dehydrated tomatoes is less than 40.

18. A method of producing a tomato paste comprising comminuting or macerating dehydrated processing tomatoes that express the cwp gene (SEQ ID NO: 2) or a polypeptide having an amino acid sequence of SEQ ID NO: 1 wherein the dehydrated processing tomatoes have been dehydrated on the vine to a Brix value in the range of 6-9 and said dehydrated tomatoes have a citric acid content below 0.6 weight % when corrected to 12 degrees Brix; and wherein the tomato paste comprises at least 0.09 weight % of GABA when corrected to 12 degrees Brix.

19. A method of producing a tomato paste comprising comminuting or macerating dehydrated processing tomatoes that express the cwp gene (SEQ ID NO: 2) or a polypeptide having the amino acid sequence of SEQ ID NO: 1, wherein the dehydrated processing tomatoes were dehydrated on the vine to a Brix value in the range of 6-9 and said dehydrated tomatoes have a citric acid content below 0.6 weight % when corrected to 12 degrees Brix; and wherein the tomato paste comprises at least 0.07 weight % of GABA when corrected to 12 degrees Brix.

20. The method of claim 19, wherein the ratio of the total amount of fructose and glucose to the amount of sucrose in said dehydrated tomatoes is less than 40.

* * * * *

SEQUENCE LISTING

```
<160> NUMBER OF SEQ ID NOS: 2

<210> SEQ ID NO 1
<211> LENGTH: 270
<212> TYPE: PRT
<213> ORGANISM: L. esculentum

<400> SEQUENCE: 1

Met Cys Ile Val Val Phe Ile Trp Glu Ala Asp Ser Arg Tyr Ser Leu
1               5                   10                  15

Val Leu Leu Leu Asn Arg Asp Glu Tyr His Asn Arg Pro Thr Lys Glu
            20                  25                  30

Val His Trp Trp Glu Asp Gly Glu Ile Val Gly Gly Lys Asp Glu Val
        35                  40                  45

Gly Gly Gly Thr Trp Leu Ala Ser Ser Thr Asn Gly Lys Leu Ala Phe
    50                  55                  60

Leu Thr Asn Val Leu Glu Leu His Thr Leu Pro His Val Lys Thr Arg
65                  70                  75                  80

Gly Asp Leu Pro Leu Arg Phe Leu Gln Ser Asn Lys Ser Pro Met Glu
                85                  90                  95

Phe Ala Lys Glu Leu Val Asn Glu Gly Asn Glu Tyr Asn Gly Phe Asn
            100                 105                 110

Leu Ile Leu Ala Asp Ile Glu Thr Lys Lys Met Val Tyr Val Thr Asn
        115                 120                 125

Arg Pro Lys Gly Glu Pro Ile Thr Ile Gln Glu Val Gln Pro Gly Ile
    130                 135                 140

His Val Leu Ser Asn Ala Lys Leu Asp Ser Pro Trp Pro Lys Ala Gln
145                 150                 155                 160

Arg Leu Lys Leu Asn Phe Lys Lys Met Leu Asp Val Tyr Glu Val Asn
                165                 170                 175

Asp Glu Lys Ile Cys Val Lys Asp Met Ile Glu Lys Leu Met Arg Asp
            180                 185                 190

Thr Thr Lys Ala Asp Lys Ser Lys Leu Pro Cys Ile Cys Ser Thr Asp
        195                 200                 205

Trp Glu Leu Glu Leu Ser Ser Ile Phe Val Glu Val Asp Thr Ala Leu
    210                 215                 220

Gly Cys Tyr Gly Thr Arg Ser Thr Thr Ala Leu Thr Ile Glu Val Gly
225                 230                 235                 240

Gly Glu Val Ser Phe Tyr Glu Leu Tyr Leu Glu Asn Asn Met Trp Lys
                245                 250                 255

Glu Gln Ile Val Asn Tyr Arg Ile Glu Lys Leu Gln Met Gln
            260                 265                 270

<210> SEQ ID NO 2
<211> LENGTH: 912
<212> TYPE: DNA
<213> ORGANISM: Lycopersicon esculentum

<400> SEQUENCE: 2
```

-continued

```
tgatcttcat cttattcttg tttttattta tagaaacaat aaaatattta taatcaatca        60
tcatgtgtat agtagtgttt atttgggaag cagatagtag atattcatta gtgttattat       120
tgaatagaga tgaatatcat aataggccaa caaaggaagt tcattggtgg gaagatggag       180
aaattgttgg tggcaaagat gaagttggtg gtggcacttg gttggcttct tcaactaatg       240
gtaaattggc ttttcttact aatgttttgg aacttcatac acttcctcat gtcaaaacta       300
gaggtgacct acctcttcga tttttacaga gcaataaaag cccaatggag tttgcaaaag       360
agttggtgaa tgaagggaat gaatacaatg ggtttaattt aattttggca gatattgaaa       420
ctaaaaaaat ggtatatgta acaaataggc ccaaggaga gcccataaca atacaagaag        480
tccaaccagg tattcatgtg ctgtccaatg caaaactgga ctctccttgg cccaaggctc       540
aaagactgaa gttaaatttt aagaaaatgt tggatgttta cgaagtgaat gacgagaaaa       600
tctgcgtcaa agatatgata gaaaaattga tgagagatac cactaaagct gataaaagta       660
aattgccttg tatttgttct acagactggg agttggaact tagctctatt ttcgtggaag       720
ttgacactgc actggggtgt tatggtacta gaagtacaac agcattgaca attgaagtgg       780
gaggagaagt aagcttttat gagttgtacc ttgagaacaa catgtggaaa gagcaaattg       840
tcaactatcg gattgaaaaa ctccaaatgc aataaatgtt tttaatatgt tgatatatct       900
aatgttttca tg                                                           912
```